United States Patent [19]

Hakim et al.

[11] Patent Number: 4,595,390
[45] Date of Patent: Jun. 17, 1986

[54] MAGNETICALLY-ADJUSTABLE CEREBROSPINAL FLUID SHUNT VALVE

[76] Inventors: Salomon Hakim, Carrera 13, N., 48-26, Bogota, Colombia; Carlos A. Hakim, 3400 Galt Ocean Dr., Apt. 1702 South, Fort Lauderdale, Fla. 33308

[21] Appl. No.: 559,864

[22] Filed: Dec. 8, 1983

Related U.S. Application Data

[63] Continuation-in-part of Ser. No. 516,137, Jul. 21, 1983, abandoned.

[51] Int. Cl.⁴ .............................................. A61B 5/00
[52] U.S. Cl. .................................... 604/9; 128/1.3; 137/530
[58] Field of Search ..................... 604/8–10; 128/1.3–1.5, DIG. 25; 137/530, 537; 251/65; 310/103

[56] References Cited

U.S. PATENT DOCUMENTS

| | | | |
|---|---|---|---|
| 3,391,289 | 6/1968 | Danilewicz | 310/103 |
| 4,156,422 | 5/1979 | Hildebrandt et al. | 604/9 |
| 4,340,038 | 7/1982 | McKean | 128/1.3 |
| 4,360,007 | 11/1982 | Levy et al. | 128/1 R |
| 4,387,715 | 6/1983 | Hakim et al. | 604/9 |
| 4,443,214 | 4/1984 | Marion | 604/9 |

OTHER PUBLICATIONS

Hakim, Salomon, "Hydraulic and Mechanical Mis-Matching of Valve Shunts Used in the Treatment of Hydrocephalus: The Need for a Servo-Valve Shunt", Dev. Med. and Child Neuro., vol. 15, No. 5, 10/73, p. 651.

Primary Examiner—C. Fred Rosenbaum
Assistant Examiner—Karen Kaechele
Attorney, Agent, or Firm—G. Roger Lee

[57] ABSTRACT

A surgically-implantable shunt valve in which the popping pressure is adjusted in finite increments by application of an external magnetic field.

33 Claims, 38 Drawing Figures

MAGNETICALLY-ADJUSTABLE CEREBROSPINAL FLUID SHUNT VALVE

BACKGROUND OF THE INVENTION

This application is a continuation in part of U.S. Ser. No. 516,137, filed July 21, 1983 and now abandoned.

This invention relates to shunt valves for venting cerebrospinal fluid ("CSF") in the treatment of hydrocephalus and similar conditions of impaired circulation and absorption of body fluids.

Cerebrospinal fluid shunt valves have been in use for over twenty years. Broadly speaking, they function by venting excess cerebrospinal fluid from the brain into the venous system or other receptive cavities (e.g., peritoneal, pleural). Many such valves, including the earliest designs, operate by controlling the amount of fluid flow. The neurosurgeon makes an estimate of the amount of flow required to relieve the hydrocephalus and selects a valve of that flow capacity. The selection is made difficult by the wide variation in normal flow rates.

About twenty years ago, applicant Salomon Hakim developed an altogether different valve, one that controlled intraventricular pressure rather than flow. That valve, which is today known as the Cordis-Hakim shunt valve, and which is described in U.S. Pat. No. 3,288,142, has been enormously successful and remains, even today, one of the most popular shunt valves in use. It has a spherical sapphire ball biased against a conical valve seat by a stainless steel spring. The pressure of cerebrospinal fluid pushes against the sapphire ball and spring in a direction tending to raise the ball from the seat. When the pressure difference across the valve (e.g., the pressure difference between the cerebral ventricle and the drainage site) exceeds a so-called popping pressure, the ball rises from the seat to vent cerebrospinal fluid. As the flow rate through the valve increases, the ball moves further away from the seat to provide a larger valve orifice, one that is always large enough that the pressure drop across the orifice never rises much above the popping pressure. Accordingly, the differential pressure across the valve remains nearly constant for any flow rate encountered within the cerebrospinal fluid system.

As successful as the Cordis-Hakim valve has been, it has one important limitation. It can only provide a fixed popping pressure. In treating hydrocephalus, it is often desirable to vary the popping pressure in accordance with ventricle size and treatment objective. For example, initial treatment may require a lower than normal pressure to initiate shrinkage of the ventricles, but as the ventricles decrease in size, the popping pressure should be increased gradually so that when the ventricles return to normal size the intraventricular pressure is at its normal value and the intracranial force systems are in balance (i.e., the popping pressure is set at a level that will stabilize the ventricles at a desired size). Generally speaking, the popping pressure should be varied inversely with the ventricle size. It is undesirable to leave a low pressure valve in a patient after the ventricles are again normal size, because the ventricles can further collapse, leading to a condition known as "slit" ventricles. A fuller discussion of these matters can be found in Hakim et al., "A Critical Analysis of Valve Shunts Used in the Treatment of Hydrocephalus", *Developmental Medicine and Child Neurology*, Vol. 15, No. 2, April 1973, pp. 230-255.

A further reason for providing adjustability in popping pressure is to correct for the wide variation in nominal popping pressure typical in manufactured valves. With an adjustable valve, the popping pressure can be more accurately set at the factory, and can be checked, and corrected if necessary, in the operating room prior to implantation. Moreover it is unnecessary to manufacture and stock valves with differing nominal pressures, as one valve can typically provide all desired pressures according to the needs at any given moment of the treatment.

Efforts have been made at developing an adjustable valve. An example is the valve disclosed in our earlier-filed copending application Ser. No. 493,748, in which an adjustment screw is turned either by a screw driver applied through the skin to the valve or by rotation of a magnet along an axis aligned with the axis of the screw.

Implantable magnetically-driven devices are known. Levy et al. U.S. Pat. No. 4,360,007 discloses an implantable actuator with a ratchet wheel, pawl, and permanent magnet; application of an external magnetic field rotates the implanted magnet and pawl to advance the ratchet wheel.

SUMMARY OF THE INVENTION

In general the invention features, in a first aspect, a surgically-implantable shunt valve in which the popping pressure is adjusted in finite increments by application of an external magnetic field. In preferred embodiments, the magnetic field causes rotation of a member, which, in turn, moves a portion of the spring biasing the ball against the valve seat; each pulse or cycle of the magnetic field causes one incremental change in the popping pressure (e.g., ten or more cycles are required to move from minimum to maximum pressure); a toothed gear is moved by a rotating escapement element, which is driven by the magnetic field; the gear is connected to a screw or cam that, in turn, changes the bias setting of the spring; in some embodiments, a ferromagnetic element or permanent magnet is mounted on an arm extending radially from said escapement element, a spring is provided to return the arm and escapement to a neutral position, and application of a single external magnetic pulse causes the arm and escapement to move away from and then back to the neutral position sufficiently to cause an incremental rotation of the gear; in other embodiments, two escapement elements are provided, each attached to a magnet and pivoted about an axis passing between the poles of the magnet; the axes of rotation of the two escapement elements are separated around the gear by a whole number of teeth plus one-half tooth; the escapement elements and magnets are either about 180° apart or about 90° apart; the external adjusting electromagnets are aligned with the magnets inside the valve; the magnetic field generated by the external electromagnets is strongest at the magnet and escapement closest to the energized magnet and thus the closest magnet is dominant and controls movement of the gear; the escapement elements have teeth on either end that mesh with the teeth of the gear; the teeth are either of the same general shape as the gear teeth (e.g., blunt) or are long, thin elements adapted to pierce through debris that collects between the gear teeth; a wheel replaces the gear and the wheel has a plurality of permanent magnets arranged around its axis of rotation, adjacent magnets having opposite polarity; the external adjusting magnets are positioned so that one is aligned with one of the permanent magnets when the other is midway between two of the permanent magnets, so that alternate energizing of the external magnets will advance the wheel one-half the angular spacing of the magnets for each energization; in some embodiments, a movable external magnet is swept by the permanent magnets (e.g., by rotation about an axis parallel to the wheel axis and radially outside the permanent magnets) to cause the wheel to rotate; and a stop is provided for the gear at a position corresponding to a known popping pressure, to permit the gear first to be adjusted against the stop and then adjusted in increments away therefrom.

In a second aspect, the invention features apparatus for applying the external magnetic field to the implanted valve. In preferred embodiments, the apparatus has either one or two electrically energizable magnets; means such as a recess mating with the skin protrusion formed by the implanted valve and an arrow indicating spinal fluid flow direction are provided to properly orient the apparatus over the implanted valve, to assure that an application of the magnetic field causes a predictable change in the popping pressure.

In a third aspect, the invention features the use of a three-arm spring in conjunction with magnetic adjustment. The spring has two flanking arms retained at their ends and a central arm that biases the ball of the valve at one end and is moved in response to the magnetic adjustment at the other end.

In a fourth aspect, the invention features a yoke for retaining such a three-arm spring. In preferred embodiments, the yoke extends alongside the inner edges of the flanking arms (to provide sideward retention for the spring) and over the top surface of those arms (to provide upward retention); the yoke is U-shaped to pass under the central arm and upwardly between the central and flanking arms; and notches are provided in flanking arms to receive portions of the yoke (to provide longitudinal retention).

The invention has the advantages of immunity to the magnetic field generated by NMR (nuclear magnetic resonance) diagnostic devices; such devices generate a steady magnet field, which cannot cause more than about one incremental change of popping pressure. It is also resistant to other incidental magnetic fields because repetitive, strong magnetic pulses are required to cause a substantial adjustment to popping pressure. The invention provides a simple, reliable, and accurate technique for noninvasive adjustment of popping pressure.

Other advantages and features of the invention will be apparent from the following description of preferred embodiments and from the claims.

DESCRIPTION OF THE PREFERRED EMBODIMENTS

STRUCTURE

Figures 1, 2, 3A, 3B, 4, 5:
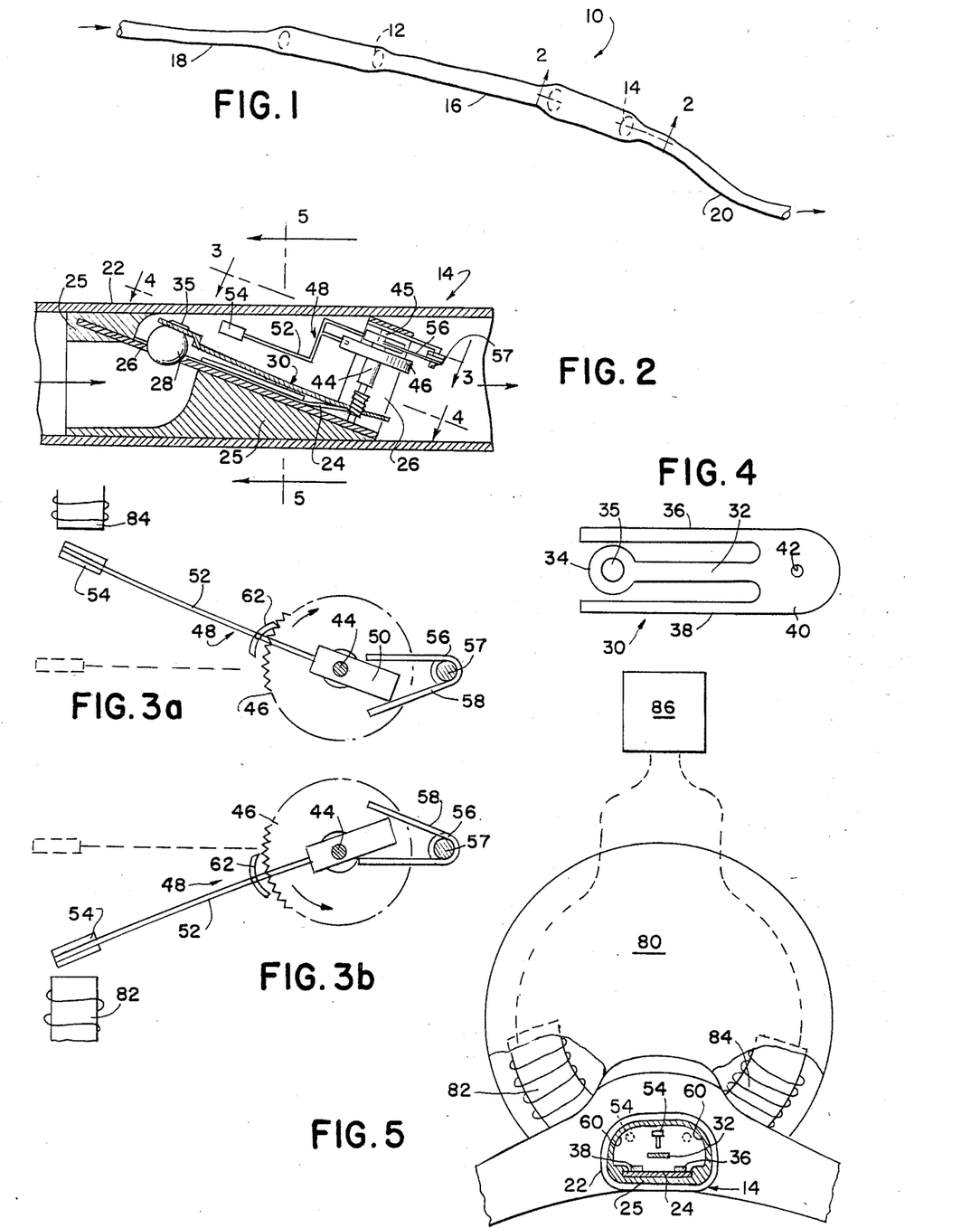
FIG. 1 is a perspective, somewhat diagrammatic, view of a first preferred embodiment of the invention.
FIG. 2 is a cross-sectional view taken at 2—2 of FIG. 1, showing the internal construction of said first embodiment.
FIGS. 3a and 3b are views taken along 3—3 in FIG. 2 showing two positions of the magnetic adjustment arm of said first embodiment.
FIG. 4 is a view taken along 4—4 in FIG. 2 of the ball biasing spring of said first embodiment.
FIG. 5 is a cross-sectional, somewhat diagrammatic, view taken along 5—5 of FIG. 2 showing the valve as it would appear installed on the skull and also showing the valve adjustment element positioned over the valve.

There is shown in FIG. 1 a shunt valve assembly 10 with two shunt valves 12, 14 separated by a pumping chamber 16. Cerebroventricular catheter 18 is connected to the inlet of the valve assembly, and drainage catheter 20, to the outlet. This assembly can be surgically implanted following well-known procedures.

A cross section through the downstream shunt valve 14 is shown in FIG. 2 (the upstream valve 12 is preferably the same except that the adjustment mechanism is absent). Valve body 22 (a surgically implantable material such as polyethersulfone or stainless steel) has within its interior an inclined plate 24 (stainless steel) held in place by molded portions 25 (plastic molded in place using forms inserted within the valve and subsequently removed). Formed in plate 24 is a circular aperture 26, the periphery of which forms a valve seat for spherical ball 28 (highly-polished sapphire). The periphery has a coined, beveled edge.

Biasing the ball against the valve seat is spring 30 (single piece of stainless steel), which is shown in plan view in FIG. 4. The spring has central arm 32 with enlarged end 34 with dimple 35 overlying and capturing ball 28. The central arm is joined to two flanking arms 36, 38 at a rear portion 40, in which there is provided hole 42 for receiving the threaded end of shaft 44.

Shaft 44 is supported at one end in a hole formed in plate 24, and at the other end in a hole formed in upper, integral extension 45 of plate 24. Fixed to the shaft at the end opposite the spring is toothed gear 46. Freely mounted to the shaft above the gear is magnetic adjustment arm 48, consisting of base 50 (stainless steel) mounted to the shaft, extension arm 52 (which extends from the base and has a step shape to pass around gear 46), and ferro-magnetic element 54 (or permanent magnet). Torsion spring 56 (stainless steel) with portions 58 flanking each side of base 50 serves to urge the arm 48 back to its equilibrium position (shown in dashed lines in FIG. 3). The torsion spring is mounted around stub shaft 57, which is secured to plate extension 45.

Turning to FIGS. 6–10, there is shown a second preferred embodiment of the invention. Assembly 100 shown in the figures would replace downstream valve 14 shown in FIGS. 1–5. A tubular plastic covering would be fitted tightly around the exterior of the assembly. A similar assembly, but absent the adjustment means, would replace upstream valve 12.

Figure 6:
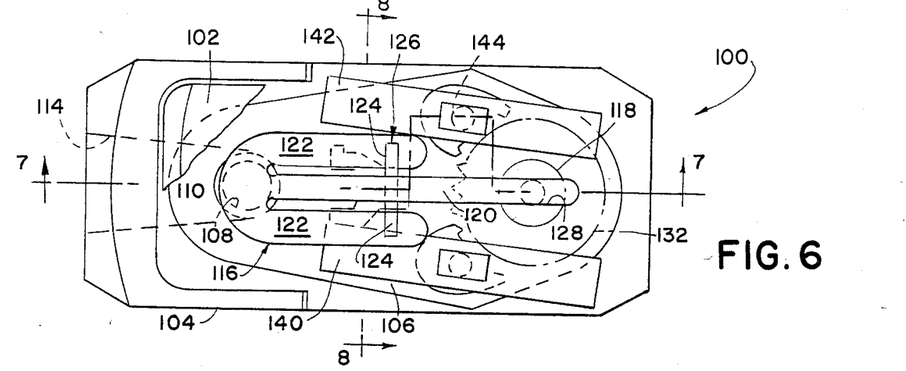
FIG. 6 is a plan view, partially cutaway, of a second preferred embodiment of the invention, showing the interior structure of the valve.
Figure 7:
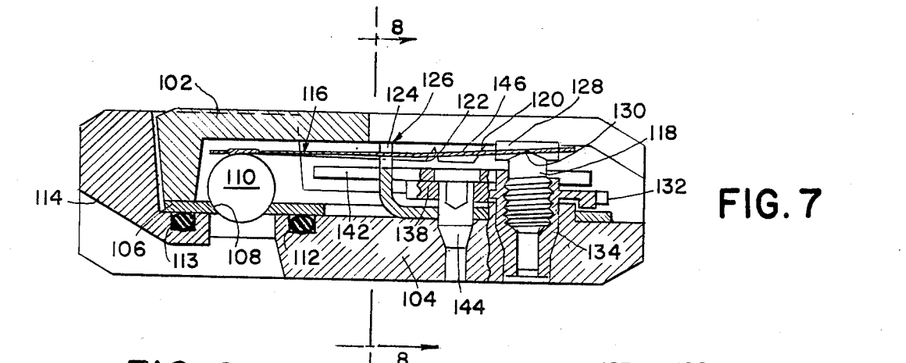
FIG. 7 is a cross-sectional view taken along 7—7 of FIG. 6.

Upper and lower housings 102, 104 (molded of plastic, a product of Bayer AG) are ultrasonically welded together so as to clamp therebetween plate 106 (stainless steel). Circular aperture 108 in plate 106 provides a valve seat for spherical ball 110 (highly-polished sapphire). O-ring 112 installed in groove 113 in lower housing 104 provides a seal between the lower housing and the plate in the vicinity of the valve seat, to ensure that all flow through the valve is through the orifice formed between ball 110 and the valve seat 108. Cavity 114 in lower housing 104 provides the flow path for fluid upstream of the valve seat.

Figure 8:
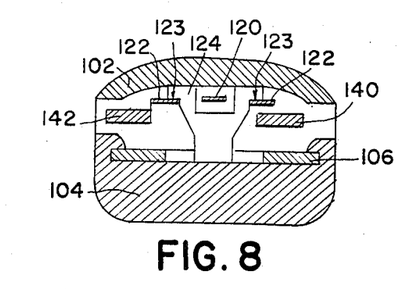
FIG. 8 is a cross-sectional view taken along 8—8 of FIGS. 6 and 7.
Figure 8A:
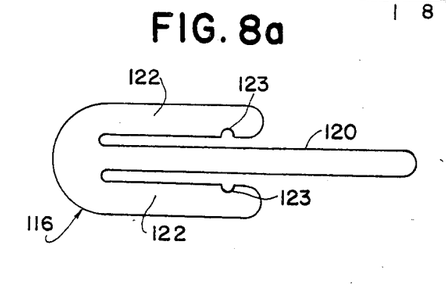
FIG. 8a is a plan view of the three-arm spring of the valve.

Ball 110 is biased against the valve seat by spring 116, which is shown in plan view in FIG. 6, and which has a central arm 120, extending from above the ball to an adjustment screw 118 at the other end of the assembly, and two flanking arms 122, the ends of which are held beneath the arms 124 of yoke 126, which is U-shaped at its upper end so as to pass around central arm 120, and which is an integral extension of plate 106 (all of which is shown most clearly in FIG. 8). Notches 123 cut in the ends of flanking arms 122 (FIG. 8a) receive the yoke arms 124, and secure the spring against longitudinal movement. The spring is secured against sideward movement by contact with the vertical outside surfaces of yoke 126.

Spring arm 120 is received in slot 128 in the head of screw 118, and rests on a wedge-shaped protrusion 130 within the slot. In that way, the screw is prevented from turning, and the force applied to the spring by the screw is transferred in a vertical direction at the center of the spring arm. The height of screw 118, and thus the amount of force applied to the spring, is adjusted by turning gear 132, which is threaded to screw 118. Gear 132 has integral shaft 134 extending into lower housing 104. Screw 118 is threaded into the interior of integral shaft 134.

Figure 9:
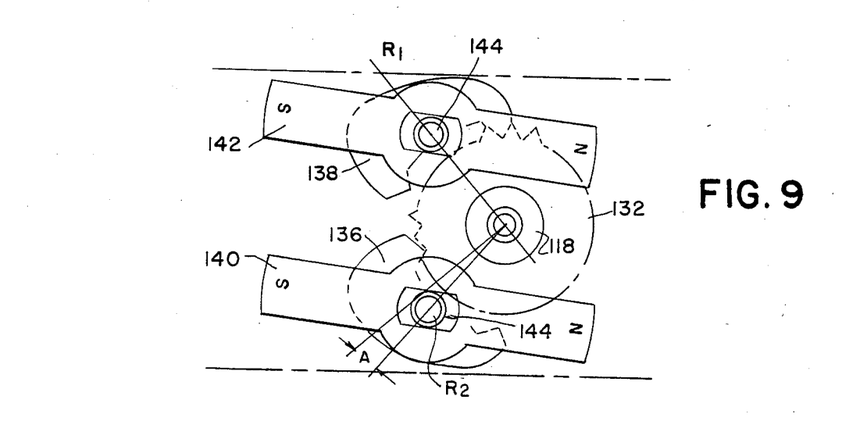
FIG. 9 is a partial plan view of said second embodiment showing only the magnetic escapement elements and gear.
Figure 10A:
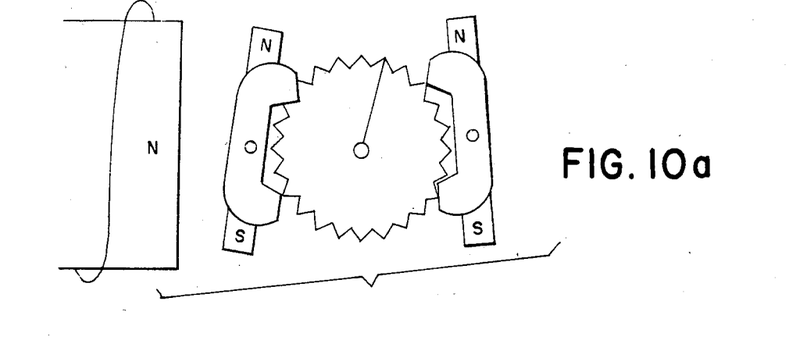
FIGS. 10a to 10d are diagrammatic plan views of the escapement mechanism of said second embodiment, showing that mechanism in four different stages in one full cycle thereof.
Figure 10B:
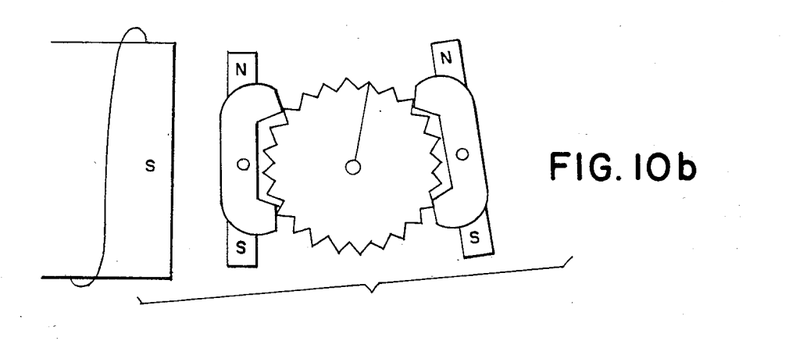
Figure 10C:
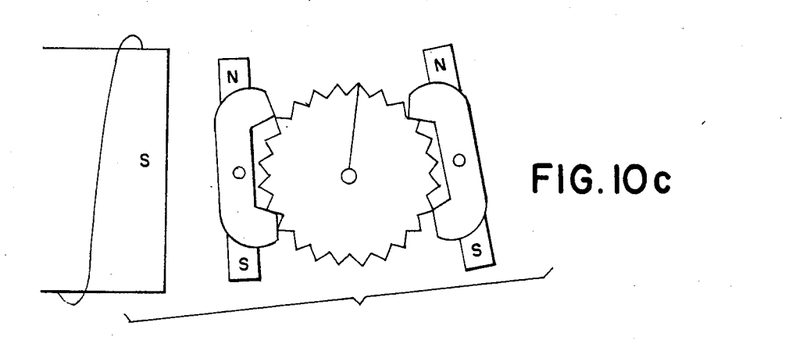
Figure 10D:
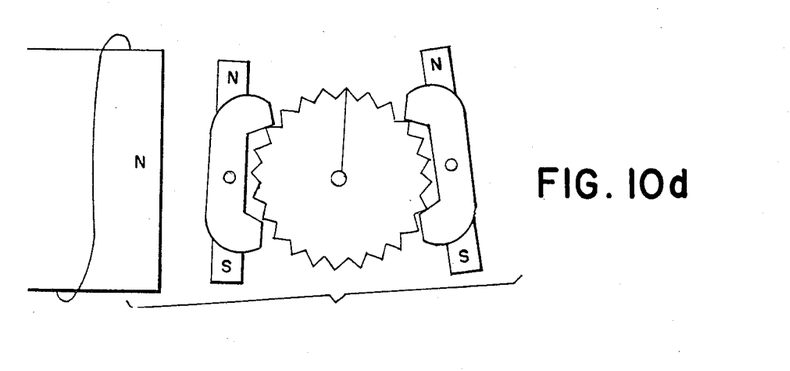

Gear 132, which has 14 teeth, is rotated by movement of escapement elements 136, 138 (best shown in FIG. 9). The escapement elements, which are mirror images of one another, are keyed to permanent magnets 140, 142, and each escapement-magnet pair is supported for free rotation on a shaft 144 supported in lower housing 104. The escapement elements are prevented from falling out of the lower housing by protrusions 146 (FIG. 7), which extend down over the heads of the shafts from upper housing 102. The centers of rotation of the escapement elements are positioned along radial lines $R_1$ and $R_2$, which are separated by an angle corresponding to a whole number of teeth plus one half of a tooth of gear 132 (the number of integral teeth can be varied, but it is preferred that there remain an additional one-half tooth separation). Both magnets 140, 142 are oriented so that their north-south axes have the same polarity and are parallel when the escapement teeth are positioned relative to the gear teeth as shown in FIG. 9.

Turning to FIGS. 17–32, there is shown another embodiment of the invention.

Figures 17, 18, 19, 20, 24, 24A, 32:
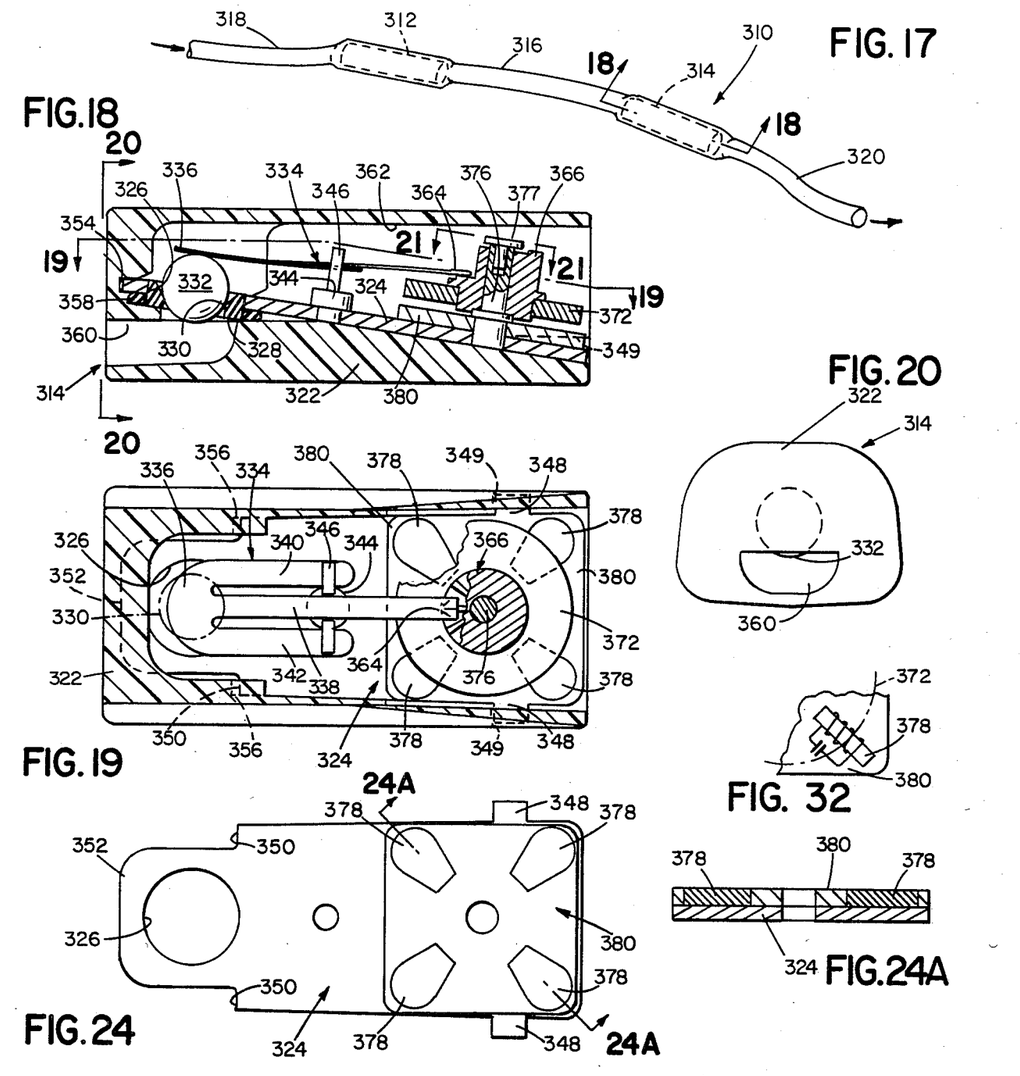
FIG. 17 is a perspective, somewhat diagrammatic, view of the most preferred embodiment of the invention.
FIG. 18 is a cross-sectional view taken at 18—18 of FIG. 17, showing the internal construction of said embodiment.
FIG. 19 is a cross-sectional view taken at 19—19 in FIG. 18.
FIG. 20 is an elevation view taken at 20—20 in FIG. 18.
FIG. 24 is a plan view of the internal support plate of said embodiment.
FIG. 24A is a cross-sectional view taken at 24A—24A in FIG. 24.
FIG. 32 is a partial plan view, somewhat diagrammatic, of an alternative embodiment wherein the stator elements each include an electrical coil.
Figure 21:
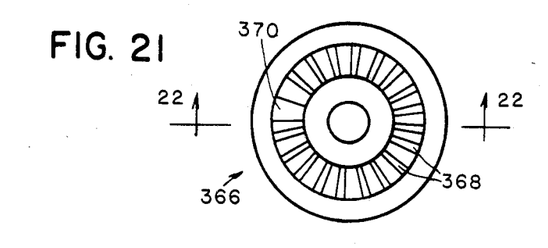
FIG. 21 is a plan view at 21—21 in FIG. 18, showing the cam of said embodiment.
Figure 22:
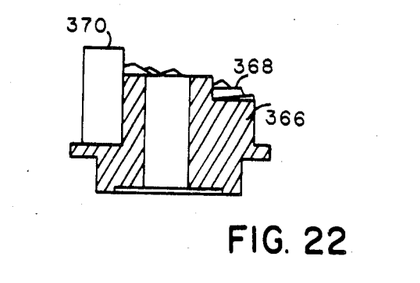
FIG. 22 is a cross-sectional view of said cam taken at 22—22 in FIG. 21.
Figure 23:
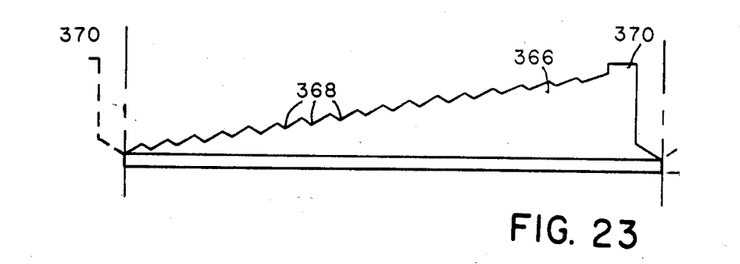
FIG. 23 is a diagrammatic view of the steps of said cam.

There is shown in FIG. 17 a shunt valve assembly 310 with two shunt valves 312, 314 separated by a pumping chamber 316. Cerebroventricular catheter 318 is connected to the inlet of the valve assembly, and drainage catheter 320, to the outlet. This assembly can be surgically implanted following well-known procedures.

A cross section through the downstream shunt valve 314 is shown in FIG. 18. The upstream valve 312 is preferably the same except that the adjustment mechanism is absent. (The tubular plastic covering shown tightly fitted around the valves in FIG. 17 is not shown in the remaining figures.) Valve body 322 (injection molded from a surgically-implantable material such as polyethersulfone) has within its interior an inclined plate 324 made from a nonmagnetic material, such as titanium or stainless steel. The plate 324 has circular aperture 326 in which is press fit a sapphire ring 328, with frustoconical surface 330 forming a valve seat for spherical ball 332 (highly-polished ruby).

Biasing the ball against the valve seat is spring 334 (single piece of stainless steel or another suitable material), shown in plan view in FIG. 19. The spring provides a low K factor to produce little change in working pressure with changes in flow (i.e., a flat flow-pressure curve). The spring has base 336 overlying ball 332, central arm 338 extending from the base to an adjustment mechanism, and two flanking arms 340, 342 extending from the base to a yoke 344. The yoke is press fit into a hole in plate 324 and tabs 346 extend over the tops of the flanking arms. The yoke is relieved in the center to provide room for the central arm to pass through. Notches (not shown) cut in the ends of flanking arms 340, 342 receive portions of the yoke, and secure the spring against longitudinal movement. The spring is secured against sideward movement by contact of the flanking arms with the vertical outside surfaces of the yoke.

Plate 324 is held tightly in place within valve body 322. The tight fit is achieved by sliding the plate into the valve body (in a direction from right to left in FIG. 18). Grooves 354, 356 at the upstream end of the valve body receive portions 350, 352 (FIG. 24) of the plate, and grooves 349 at the downstream end receive tabs 348 on the plate. The grooves extend generally horizontally rather than in the inclined direction followed by the plate, and thus the tabs 348 and portions 350, 352 tend to become tightly wedged into the grooves.

Grooves 354, 356 at the ball end of the valve body also serve to press plate 324 downwardly so as to squeeze it tightly against O-ring 358 (silicone rubber), which provides an internal seal to ensure that all flow through the valve is through the orifice formed between the ball 332 and the valve seat 330. Flow through the valve is from inlet cavity 360, past ball 332, and into outlet cavity 362.

The preload of spring 334 against ball 332 is adjusted by using cam 366 (Delrin) to vary the vertical position (through a 0.75 mm range) of free end 364 of central arm 338. The spring preload establishes the pressure of the valve. The cam (best shown in FIGS. 21-23) has a circular staircase of eighteen steps, each being grooved so as to have a V-shape cross section. Free end 364 of arm 338 has a similar V-shape chosen to mate with the V-shape of steps 368. At each end of the staircase a barrier is provided by element 370. This confines rotation of the cam to slightly less than one revolution. The V-shape of steps 368 act as detents to keep the cam in precisely one of eighteen possible angular positions. That means that the vertical position of free end 364 of arm 338 is always at precisely one of eighteen different values and, in turn, that the working pressure of the valve is always at one of eighteen possible levels.

Figure 25:
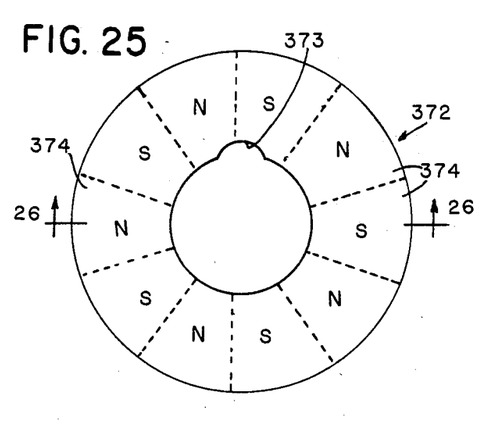
FIG. 25 is a plan view of the permanent-magnet disk of said embodiment, showing the ten pairs of poles on said disk.
Figure 26:
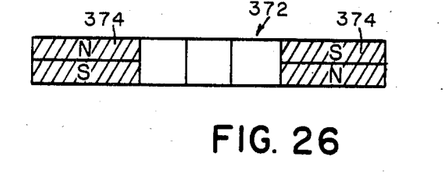
FIG. 26 is a cross-sectional view of said disk taken at 26—26 in FIG. 25.

Cam 366 is press fit into the central hole in rotor 372 (4 mm diameter), with a protrusion on the cam fitting into recess 373 in the rotor to assure accurate angular positioning. The cam-rotor unit rotates loosely on shaft 376, the base of which is press fit into plate 324. The unit is retained by retaining element 377 secured to the top of the shaft. The rotor is preferably made of platinum cobalt or samarium cobalt (which may be plated with platinum to improve corrosion resistance). The rotor has ten permanently magnetic poles 374 of alternate polarity (FIGS. 25-26). At any one angular position, the pole exposed on the top surface of the disk is opposite that of the one exposed on the bottom surface.

Below rotor 372 there are fixed in place four stator elements 378 each made of a material that is magnetically soft and permeable, and that is resistant to corrosion in the presence of cerebrospinal fluid, which contains chlorides. Preferred materials include magnetic stainless steel alloys and alloys of nickel, iron, and molybdenum or cobalt. As shown in FIG. 8, the stator elements are embedded in a plastic member 380, which is fixed to plate 324 by means of shaft 376. The stator elements are shaped so that the portion of each lying beneath the rotor matches the size of permanent magnets 374. The portions of the stator elements lying radially beyond the rotor are sized to match the area beneath the rotor so that the boundary between poles, when the stator is magnetized, is at the perimeter of the rotor.

Operation

In operation the shunt valve assembly is surgically implanted in a patient following well-known procedures. Before implantation the pressure of adjustable valve 314 can be set to the desired level according to the circumstances of the case. For instance, it can be set approximately equal to the patient's pre-operative ventricular CSF pressure so that no immediate pressure change occurs as a result of the operation. After the patient has recovered from the trauma of the operation, the pressure is adjusted downwardly to the desired level. In the case of normal-pressure hydrocephalus, the pressure is lowered to a level sufficient to initiate shrinkage of the cerebral ventricle. Further adjustments in pressure can be made at subsequent times, as necessary. In the typical treatment of normal-pressure hydrocephalus, the pressure would be adjusted upwardly after sufficient shrinkage of the ventricle has occurred in order to stabilize ventricle size.

In children at the beginning of the treatment, the pressure should be lowered to a level inversely proportional to the ventricle size to reduce stress on the brain parenchyma (see FIG. 13 of Hakim et al., "The Physics of the Cranial Cavity", Surg. Neurol., Vol. 5, March 1976), and as the ventricle decreases in size the pressure of the valve should be increased, so when the ventricle attains normal size the intraventricular pressure is again normal, thereby avoiding development in the patient of a slit-ventricle condition. Also in cases of normal-pressure hydrocephalus, sometimes in spite of a low-pressure valve the patient does not improve and the ventricle size remains unchanged, making the surgeon think he is dealing with a case of brain atrophy. But by further changing the valve pressure to a lower one, the ventricle decreases in size and the patient immediately starts to improve. In elderly persons and in long standing cases of normal-pressure hydrocephalus, it has been found that the intraventricular pressure needs to be lowered more than in young people and in hydrocephalus of short duration.

Another advantage of the invention arises in the procedure for determining when an implanted shunt valve can safely be removed from a patient, i.e., determining whether the patient is still dependent on the valve for drainage of excess cerebrospinal fluid. The conventional technique for making that determination has been to temporarily pinch closed the tube downstream of the valve and observe the patient for symptoms (e.g., slight headache) indicative of valve dependency. In the absence of symptoms the valve can be removed. With the invention it is unnecessary to stop flow entirely. A safer procedure can be followed. Valve pressure is raised, slightly at first, more so later for confirmation, using the adjustment mechanism.

Turning to the embodiment of FIGS. 1-5, valve pressure adjustments are made by applying a pulsed magnetic field to the vicinity of the shunt valve as shown diagrammatically in FIG. 5. A valve adjustment element 80 is applied over adjustable valve 14 in the orientation shown. The adjustment element 80 contains two electromagnets 82, 84, which are separately controlled by an external control device, shown diagrammatically at 86. The adjustment element has a marking (such as an arrow pointing in the direction of CSF flow) on its exterior to assure that it is applied to the valve in the correct orientation. Control device 86 has controls that permit the operator to choose the direction of adjustment, i.e., higher or lower pressure, and the amount of adjustment. The direction of pressure adjustment is determined by which of the two magnets 82, 84 is energized. The amount of adjustment is determined by the number of pulses applied to the selected magnet. Each application of a pulse causes magnetic arm 48 to move toward the interior face 60 of the valve housing, and then back to its neutral position, as shown in FIGS. 3a and 3b, which illustrate the two directions of movement of the arm. In FIG. 3a, magnet 84 is energized, and the arm is moved between its neutral position and the extreme (upper in the figure) position shown. Travel of the arm is stopped by contact of the magnet 54 with interior surface 60 (FIG. 5) of the valve housing. In FIG. 3b movement in the opposite direction is shown. Each cycle of arm 52 causes escapement element 62 to engage a tooth of gear 46 and thereby rotate the gear through a small angle. Arm 52 bends slightly during the cycle to permit the escapement element to so engage. Torsion spring 56 provides a restoring torque to the arm. Each electrical pulse supplied to the magnets has a shape selected to move arm 52 slowly out of and back into its neutral position, so that there is little or no overtravel of the arm beyond neutral, thus avoiding undesired reverse rotation of gear 46.

The embodiment of FIGS. 6–10 is surgically implanted in the same manner as the first-described embodiment.

Adjustments are made to the popping pressure using an adjustment element and control device of the type shown in FIG. 5 for the first embodiment. A magnetic field which alternates polarity with each pulse is applied from one or the other side of the valve assembly. Both magnets 140, 142 are influenced by the field, but the magnet that is closest to the source of the field dominates the other due to the fact that the strength of a magnetic field decreases as the square of the distance from its source. Thus, for purposes of understanding operation of the valve, it can be assumed that only the magnet closest to the source of the field is driven. The time-variation in the strength of the magnetic field is selected to cause the magnet, and the escapement element connected to it, to rotate back and forth sufficiently to cause gear 132 to rotate by the angle corresponding to one tooth for each full cycle of the escapement element.

Shown in FIGS. 10a–10d are diagrammatic views of four stages during one cycle of the escapement element. When the electromagnet is energized with north polarity, this causes the escapement magnet to rotate; the south pole of the escapement magnet is attracted toward the electromagnet, and the north pole is repelled away therefrom. In the figures, the gear has more teeth than in the preferred embodiment, and the escapement elements are shown diagrammatically.

Rotation of gear 132 causes screw 118 and, in turn, one end of spring arm 120, to move upwardly or downwardly. This, in turn, changes the force applied by spring 116 to ball 110, and thus the popping pressure at which fluid pressure on the ball will lift it away from the valve seat. The advantages of using the type of spring shown are that a very low K-factor (spring rate) can be provided at the ball (and thus little change in popping pressure for change in flow rate) and the bias force on the ball is less sensitive to changes in the height of screw 118 than would be another type of spring (thus allowing finer adjustment of popping pressure). One full revolution of the gear comprises the full extent of ordinary adjustment of the popping pressure.

The embodiment of FIGS. 17–32 is surgically implanted in the same manner as the first-described embodiment.

Figure 27:
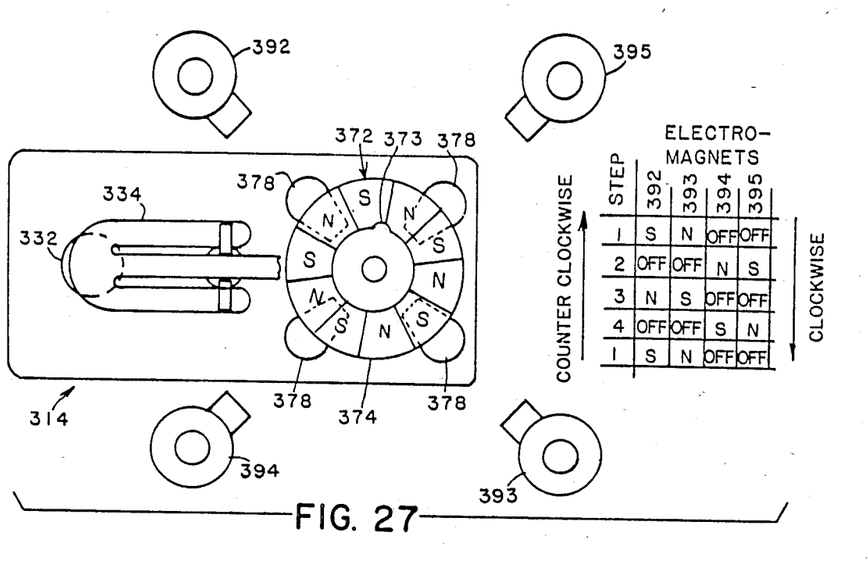
FIG. 27 is a diagrammatic view of said embodiment in which the positions of the external adjusting electromagnets are shown (much smaller than actual size).
Figure 28:
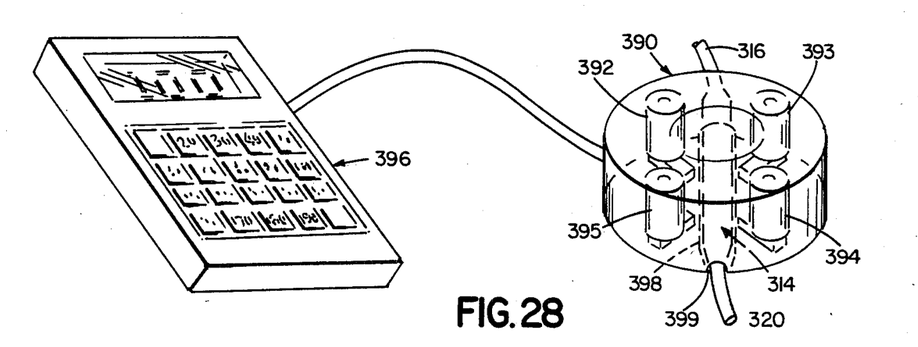
FIG. 28 is a diagrammatic view of said embodiment implanted beneath the scalp and covered by an external adjustment element.
Figure 29:
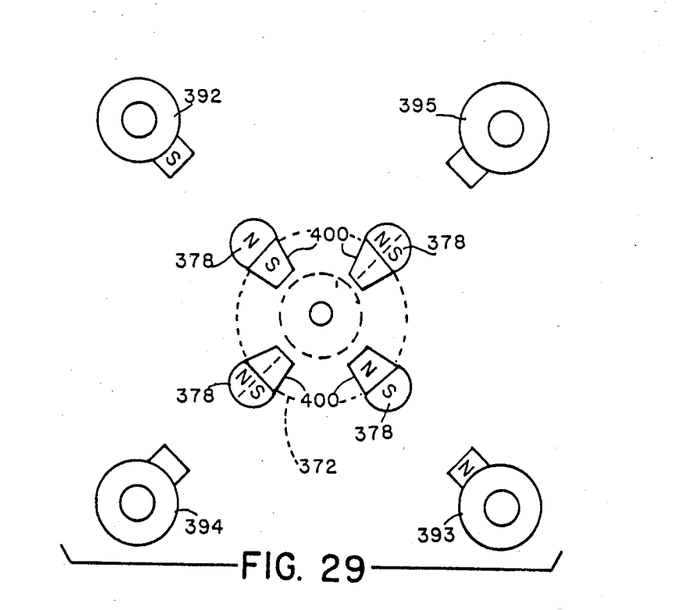
FIG. 29 is a diagrammatic view similar to FIG. 27 except that the rotor and cam have been removed to show the magnetic polarization of the four stator elements.

Valve pressure adjustments are made by applying a pulsed magnetic field to the vicinity of the shunt valve as shown diagrammatically in FIGS. 27–29. A valve adjustment element 390 is applied over adjustable valve 314 in the orientation shown. The adjustment element contains four electromagnets 392, 393, 394, 395, which are separately controlled by an external control device, shown diagrammatically at 396. Adjustment element 390 has a marking (such as an arrow pointing in the direction of CSF flow) on its exterior to assure that it is applied to the valve in the correct orientation, and it has a groove 398 in its bottom surface sized to fit over the protrusion in the scalp, at the site of the implanted valve. The groove is narrowed at one end 399 to enable correct longitudinal alignment relative to the adjustable valve 314.

Control device 396 has input keys, which the operator uses to select one of 18 possible desired pressures (from 20 to 190 mm $H_2O$) and a pressure display.

Each of electromagnets 392, 393, 394, 395 can be energized to have either the north or south polarity facing the stator elements, or each can remain off altogether. Movement of rotor 372, in the desired direction and through the desired angle, is achieved by energizing the electromagnets in the sequence shown in the table in FIG. 27. For example, clockwise motion is achieved by first energizing electromagnets 392, 393 to south and north polarities, respectively, and leaving electromagnets 394, 395 off. In the next step electromagnets 392, 393 are left off, and electromagnets 394, 395 are energized to north and south polarities, respectively. The sequence repeats itself after the fourth step. Rotor 372 is shown in FIG. 27 in the position reached after the first step (the polarities of the rotor magnets are those on the bottom surface). If the magnetic field provided by the electromagnets is described by a vector pointing from the south to the north pole of the energized magnets, then it can be seen that the sequence prescribed for causing rotor 372 to rotate clockwise (down the table in FIG. 27) amounts to rotating the field vector in the counterclockwise direction (opposite that of the rotor), in 90° steps.

Electromagnets 392, 393, 394, 395 are positioned 90° apart and spaced equal radial distances from a central axis. When adjustment device 390 is installed properly over valve 314, the central axis of the electromagnets is coincident with the axis of rotation of rotor 372, and each electromagnet is aligned at the same angular position as one stator element 378. It is not, however, necessary that this alignment be exact. The invention is tolerant of alignment errors, which are unavoidable owing to the inability of the user to see rotor 372 or stator elements 378 and to the small size of those elements relative to the size of the external electromagnets.

The magnetic polarization induced in the stator elements 378 as the result of energizing the electromagnets is diagrammatically illustrated in FIG. 29. The two stator elements along the axis connecting the two energized electromagnets are polarized in the radial direction, so that the boundary between the poles lies roughly at the peripheral edge of disk rotor 372. The radially inner portions of these two stator elements, the portions lying beneath rotor 372, have the opposite polarity of the portions lying outside. By contrast, the stator elements along the other axis are polarized so that the boundary between poles lies along the radial direction. Both poles extend beneath the rotor 372. This pattern of polarization will result even if there is substantial error in the orientation of the electromagnets.

Movement of rotor 372 is influenced predominantly by the stator regions 400 (shown in FIG. 29) lying beneath the rotor, as it is those portions that are closest to the permanent magnets 374 of the rotor. Accordingly, the part of the stator elements with uniform polarity dominate over those with split polarity. This phenomenon could be emphasized by making the stator elements of a magnetically anisotropic material so that the magnetization induced by the external electromagnets is strongest along the radial axis of the corresponding stator elements.

The number of magnetic poles 374 is selected so that when one pair of radially opposite stator elements 378 is aligned with one pair of magnetic poles 374 (as are the upper left and lower right stator elements in FIG. 27) the other two stator elements (the upper right and lower left in FIG. 27) are each staggered halfway between two of the poles 374. In operation, control device 396 energizes the electromagnets closest to the pair of stators staggered between two magnets, thereby causing the rotor to move through an angle corresponding to one half the width of a magnetic pole 374.

In the preferred embodiment there are ten magnetic poles on each side of the disk, and thus twenty angular increments in one full revolution (i.e., each step is one twentieth of 360°, or 18°). Only eighteen of these increments are used, corresponding to the eighteen detented steps along the staircase surface of cam 368 (the other two increments are occupied by the detent wall 370 of the cam).

After a pressure is prescribed on control device 396, an enter key is pressed. That initiates a sequence of eighteen steps in the direction of lower pressure settings, counterclockwise rotation of rotor 372. This assures that the cam is returned to a position wherein spring arm 364 is at the lowest step on the cam staircase. If fewer than eighteen steps are actually needed to bring the cam to this position (as will most often be the case), the detent wall provided by element 370 of the cam prevents further rotation. After the eighteen-step resetting sequence is complete, the rotor is moved clockwise by the number of steps corresponding to the prescribed pressure.

Various variations can be made to the embodiment of FIGS. 17–32.

A magnetically anisotropic material could be used for the stator elements, with the strongest axis of magnetization oriented along the radial direction. Such anisotropy could also be achieved mechanically by splitting each stator element along the radial direction into two or more segments.

A variable reluctance or hybrid rotor could replace permanent-magnet rotor 372.

Linear movements within an implanted device could be achieved following the invention by providing a linearly-moving element as the rotor and by placing stator elements along the path of the linearly-moving rotor.

A rotor with fewer poles could replace the ten-pole rotor of the preferred embodiment, particularly where fine angular precision is not required (e.g., in a pump a simple two-pole rotor might suffice). Strong permanent magnets could be used to apply the external field (e.g., in the two-pole rotor of the pump application just described).

Electrical wire could be wrapped around the implanted stator elements forming a coil so that an electrical current is induced therein by the externally-pulsed magnetic field; the electrical current would in turn magnetize the stator elements if the coil circuit is closed by a resistor or a capacitor.

Figure 30:
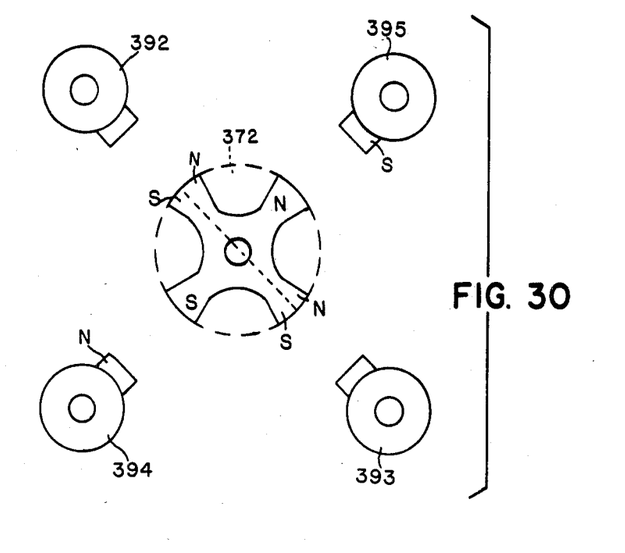
FIGS. 30 and 31 show the magnetic polarization of an alternative embodiment, where a one-piece stator element is used.
Figure 31:
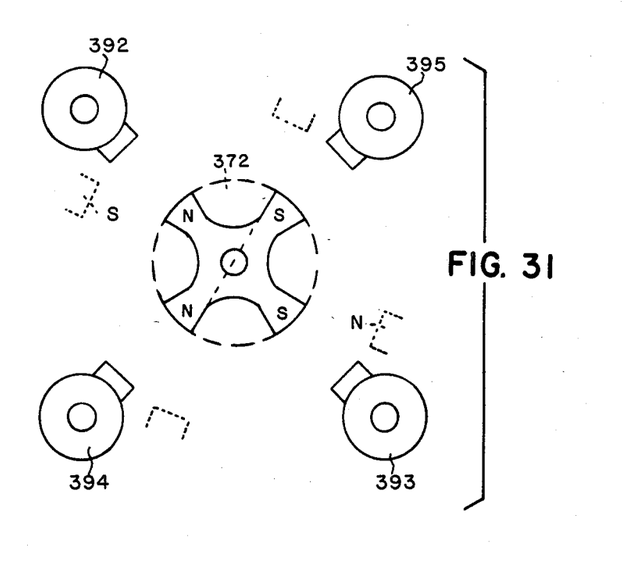

A single-piece stator element, e.g., with four lobes as shown in FIG. 30, could replace the stator elements of the preferred embodiment. An advantage of using a single-piece stator element is that the stator can lie entirely inside of the outer perimeter of the rotor, and thus provide for a more compact implanted unit. This is because, when magnetized, as shown in FIG. 30, the dominating lobes are all of one polarity, rather than split radially into two polarity regions as in the preferred embodiment. Thus the entire lobe, not just the inner half, can be influential in moving the rotor. The disadvantages of the single-piece stator is its lower tolerance to errors in alignment of the external magnetic field. The reduced tolerance for misalignment can be understood by reference to FIG. 31, in which the external field has been rotated sufficiently to cause the lobes that were split into two poles to now be entirely within the region of one pole. As a result all four lobes have nearly equal influence on the rotor, and it is not possible to move the rotor.

A presently even more preferred embodiment is one having a rotor 372 with six poles rather than ten (as shown in the figures). Such a rotor provides twelve steps of 30° for one full revolution. Eleven of these can be used to provide eleven different pressure settings (each differing by 15 mm $H_2O$) from 30 to 180 mm $H_2O$. An advantage of six poles is that with the four-stator-element configuration (FIG. 27) greater torque is available using six rather than ten poles. This results because all four stator elements, when magnetized by the external field, generate a torque in the same direction. In the ten-pole embodiment (FIG. 27), this is not the case. The torque generated by the stator elements with split polarity (upper right and lower left in FIG. 29) is opposite, though weaker than, that generated by the stator elements with uniform polarity. It is instructive to note, however, that this difference between the six and ten-pole embodiments is just the opposite if a one-piece, four-lobed stator is used. In that case, the split polarity stator elements generate opposing torque with the six-pole rotor and not with the ten-pole one. Also, if a ten-pole rotor is used with separate stator elements, torque can be increased by using anisotropic material for the stator elements, as that will increase the dominance of the uniform polarity stator elements over the split polarity ones.

Other Embodiments

Other embodiments are within the scope of the following claims.

Figure 11:
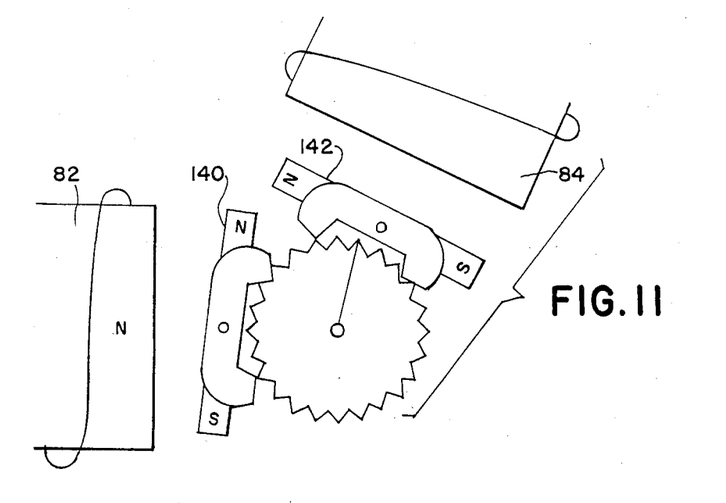
FIG. 11 is a partial plan view of a preferred variation of the gear and escapement portion of said second embodiment.

Another construction is shown in FIG. 11. One of magnets 140, 142 (and the associated escapement element) is positioned approximately 90° around the gear from the other magnet so as to be approximately normal to the other magnet. The valve adjustment element for use with this valve is modified so that external electromagnets 82, 84 are also positioned at roughly 90° to one another (as suggested in FIG. 11). The 90° orientation helps increase the dominance that one of magnets 140, 142 has over the other when only one of external electromagnets 82, 84 is energized.

Figure 12:
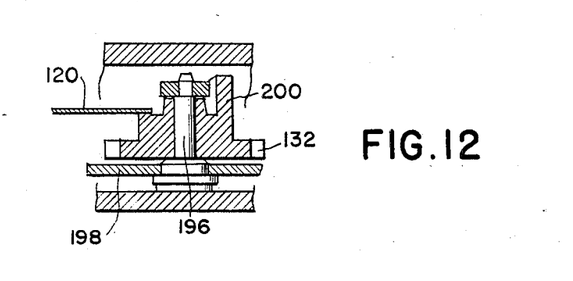
FIG. 12 is a partial sectional view of a preferred variation of the cam and gear of said second embodiment.

Another variation that is preferred is the use of a cam 200, as shown in FIG. 12, instead of screw 118, to adjust the height of spring arm 120 in response to rotation of gear 132. Others are to use fewer teeth (e.g., fourteen) on gear 132, to provide a stop for gear 132 (e.g., a pin extending from the gear and abutting a tab) to stop its rotation at positions corresponding to the minimum and maximum popping pressures, and to mount gear 132 and the escapement elements on stub shafts 196 pressed through plate 198 (equivalent to plate 106 of FIG. 7). The stop is useful during adjustment; e.g., gear 132 can be rotated counterclockwise until it reaches the stop and then a desired number of clockwise rotational increments can be prescribed therefrom, to provide a repeatable, accurate setting of popping pressure.

Figure 13:
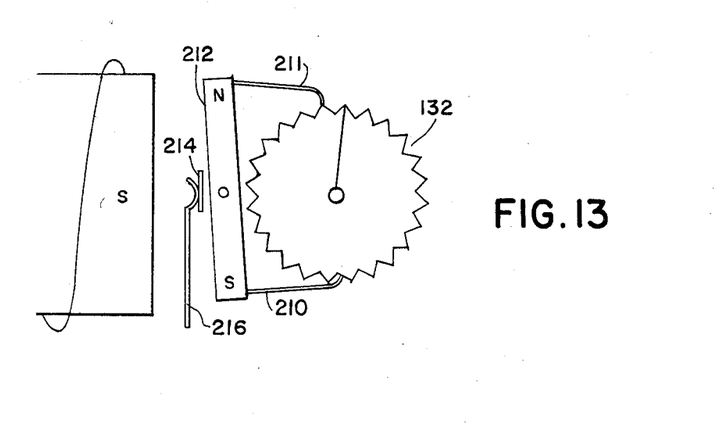
FIG. 13 is a diagrammatic view of the gear and escapement element of another variation of said second embodiment.

Instead of using two escapement elements of the type shown in FIGS. 10a–10d it may be preferred to use only one escapement element of the type shown in FIG. 13. The blunt teeth of the FIG. 10 escapement elements have been replaced by thin, flexible elements 210, 211, attached at either end of single magnet 212. This construction is better able to accommodate debris that may collect in the valve, as thin elements 210, 211 are better able than blunt teeth to pierce through any debris that might collect between the gear teeth. Each pulse of an externally-applied magnetic field has the effect of momentarily rotating magnet 212 against the torsional centering spring formed by plate 214 and spring 216, and thereby rotating gear 132 by the angular separation of its teeth. The element doing the pushing (e.g., element 210 in FIG. 13) during the movement remains relatively rigid, and thus overcomes the much smaller retarding force of the other element (e.g., element 211 in the figure), which tends to bend out of the way of the gear teeth. At the end of each pulse, the centering spring 216 brings magnet 212 and elements 210, 211 back to the rest position.

Figure 14:
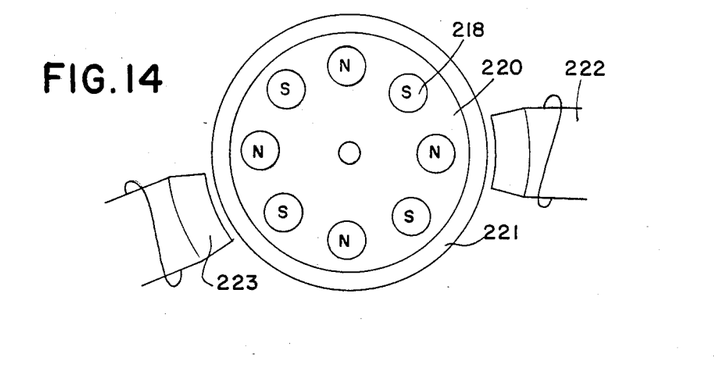
FIGS. 14, 15, and 16 are diagrammatic views of the magnet wheels and external adjusting magnets of three other embodiments.

Another embodiment uses a very small stepper motor similar to the type used in electronic watches in place of the disclosed mechanisms for rotating the spring adjustment screw; the rotor of the stepping motor would reside in the valve, and the stator would be placed in the external adjustment element. (This contrasts with the embodiment of FIGS. 17–32, wherein part of the stator resides in the valve.) Such an arrangement is shown in FIG. 14. A plurality of alternate polarity permanent magnets 218 are formed on disk 220 (samarium-cobalt); one pole of each magnet 218 is on the top surface of the disk; the other pole is on the bottom surface. The disk 220 is attached to a wheel 221, that replaces gear 132, to form the rotor portion of the stepper motor. External electromagnets 222, 223 are positioned as shown in FIG. 14 with respect to disk 220; when one external electromagnet 222 is aligned with one of magnets 218, the other external electromagnet 223 is staggered halfway between two of magnets 218. In operation, electromagnets 222, 223 are pulsed alternately, so that the electromagnet pulsed is the one staggered between two of magnets 218. The direction of rotation of the disk 220 will be determined by the polarity of this magnet. This embodiment generally requires a large rotor and accurate positioning of the external stator.

Another variation is to use a pair of permanent magnets attached at diametrically opposed locations on a wheel that would replace the toothed gear of the disclosed embodiments. An external horseshoe magnet would be aligned with the magnets on the wheel and would then be turned to make a pressure adjustment.

Figure 15:
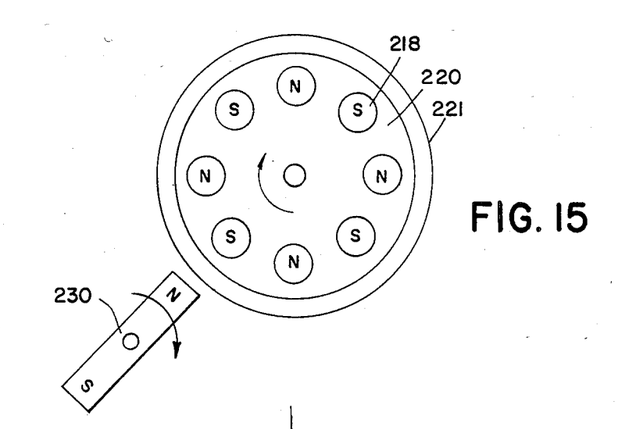

Another variation would be to provide wheel 221, disk 220, and circular array of permanent magnets 218 described in connection with FIG. 14, but to rotate wheel 221 by rotating an external magnet 230 positioned as shown in FIG. 15. Each revolution of adjusting magnet 230 advances wheel 221 by the angular separation between two of magnets 218. The rotating magnet 230 could be replaced by other mechanisms designed to move a magnetic field along a generally circumferential direction past magnets 218; e.g., a coil magnet could be repetitively swept past disk 220 by action of a solenoid and return spring, with the coil magnet being energized only when moving in one direction.

Figure 16:
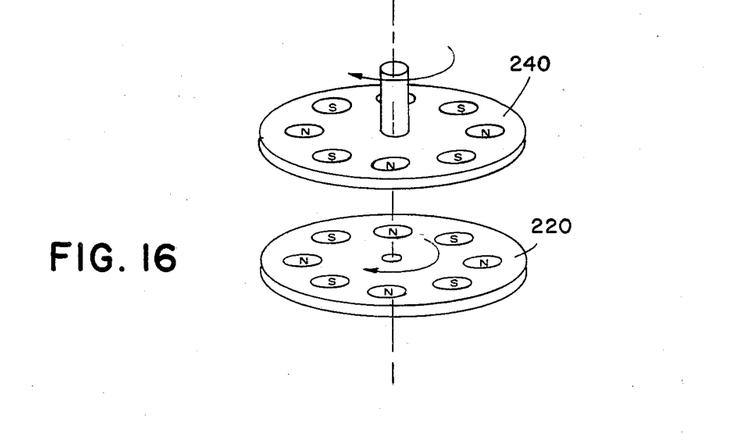

Another variation is shown in FIG. 16. The external adjusting device is a disk 240 (samarium-cobalt) having the same array of permanent magnets as on disk 220 inside the valve. Identity of the arrays makes possible turning the internal wheel in synchronism with rotation of the external disk.

What is claimed is:

1. A surgically-implantable shunt valve for venting cerebrospinal fluid in the treatment of hydrocephalus and for shunting other body fluids, said valve comprising a housing constructed of a surgically-implantable material, an inlet and outlet chamber within said housing, said housing including inlet and outlet ports communicating with said inlet and outlet chambers respectively for connecting said inlet and outlet chambers to external catheters or other fluid conduits, an aperture communicating between said chambers, said aperture having a circular periphery forming a circular valve seat, a valve element of diameter larger than said circular valve seat, spring means for biasing said valve element against the circular valve seat so as to keep said aperture closed until the cerebrospinal fluid pressure in said inlet chamber exceeds a preselected popping pressure and so as to open said aperture when said popping pressure is exceeded so as to vent cerebrospinal fluid through said aperture into said outlet chamber, and incremental magnetic adjustment means for increasing or decreasing the amount of said bias in finite increments in response to pulses of a magnetic field applied from outside the body ao as thereby to increase or decrease said popping pressure in finite increments, said incremental magnetic adjustment means comprising a primary member adapted to cooperate with said spring means so as to increase or decrease said bias when said primary member is moved, said primary member not being itself susceptible to movement by said external magnetic field, and a secondary member susceptible to said applied magnetic field and mounted and positioned with respect to said primary member so as to be capable of movement relative to said primary member and so as to cause no more than an incremetal movement of said primary member for each pulse of said magnetic field.

2. The valve of claim 1 wherein said spring means comprises a three-arm spring having two flanking arms and a central arm, one end of said central arm being positioned to bias said ball against said circular valve seat, and the other end of said central arm being said portion of said spring means.

3. The valve of claim 5 wherein spring means are provided for returning said escapement element and arm to a neutral position.

4. The valve of claim 3 wherein said arm, escapement element, gear and spring means are adapted so that application of a varying magnetic field that rises and then decays has the effect of moving said arm through a cycle consisting of movement in one direction from said neutral position to a stop position and then back again and so that as the result of said movement said gear rotates through a finite angle, said spring portion is raised or lowered a finite distance, and said popping pressure is varied by a finite amount.

5. The valve of claim 4 wherein said escapement element is mounted on an arm, said arm is pivoted about an axis, and a ferromagnetic or permanently magnetic material is attached to said arm at a radial location further from said pivot than said escapement element.

6. The valve of claim 5 wherein more than ten such cycles are required to raise said popping pressure from its minimum to its maximum.

7. The valve of claim 1 wherein there are two said escapement elements engaging said gear at different angular positions about the gear.

8. The valve of claim 7 wherein said two escapement elements are each connected to a permanent magnet and each escapement/magnet pair is pivoted about an axis passing between the two poles of the magnet.

9. The valve of claim 8 wherein the angular locations of he axes of rotation of said escapement elements are separated angularly around said gear by a whole number of gear teeth plus one half of a tooth.

10. The valve of claim 9 wherein said two escapement elements are positioned about 180° apart around said gear.

11. The valve of claim 10 wherein for each said magnet the line connecting the poles of said magnet is generally parallel to said line on the other of said magnets.

12. The valve of claim 9 wherein said two escapement elements are positioned about 90° apart around said gear.

13. The valve of claim 12 wherein for each said magnet the line connecting the poles of said magnet is generally normal to said line on the other of said magnets.

14. The valve of claim 13 wherein said escapement elements are positioned so that an external magnetic field can be applied in a first location such that the field provides a stronger turning moment on one said escapement than the other, and so that if said external field is applied in a second location a stronger turning moment will be provided to the other of said escapements.

15. The valve of claim 1 wherein stop means are provided for stopping movement of said primary member at a position corresponding to a known popping pressure, to thereby permit pressure adjustments to be made by first causing said member to move against said stop and then incrementally moving said member away from said stop.

16. The shunt valve of claim 1 in combination with apparatus for providing a pulsed magnetic field to adjust the said shunt valve, said apparatus comprising an electromagnet and means for orienting said apparatus and thereby said magnet in a predetermined orientation with respect to said valve so that energization of said electromagnet will have a predictable effect on the popping pressure of said valve.

17. The apparatus of claim 16 wherein said means for orienting comprises a recess shaped to fit over the protrusion formed on the skin surface by said valve when implanted.

18. The apparatus of claim 17 wherein said means for orienting comprises an arrow or other indicia indicating the direction of fluid flow so that the user can orient said apparatus so that said arrow points in the direction of spinal fluid flow through said valve.

19. The apparatus of claim 16 wherein said apparatus comprises two electromagnets, each separately energizeable and each oriented differently than the other so that upward adjustment of said popping pressure is achieved by energizing one of said electromagnets and so that downward adjustment is achieved by energizing the other of said electromagnets.

20. The shunt valve of claim 1 wherein
said spring means comprises a spring having a low spring rate to make said popping pressure substantially independent of changes in fluid flow rate, and
said incremental magnetic adjustment means comprises means for increasing or decreasing said bias without substantially affecting the spring rate of said spring.

21. The shunt valve of claim 1 wherein
said spring means comprises a three-arm spring having two flanking arms and a central arm, one end of said central arm being positioned to bias said valve element against said circular valve seat, and
said magnetic adjustment means comprises means for raising or lowering the other end of said central arm with respect to said valve element so as thereby to increase or decrease said bias on said valve element and thus said popping pressure.

22. The shunt valve of claim 1 wherein
said spring means comprises a three-arm spring having two flanking arms and a central arm, one end of said central arm being positioned to bias said valve element against said circular valve seat, and the ends of said flanking arms being retained by a yoke that extends over the upper surfaces of said ends to retain said ends against upward movement, and
said magnetic adjustment means comprises means for raising or lowering the other end of said central arm with respect to said valve element so as thereby to increase or decrease said bias on said valve element and thus said popping pressure.

23. The valve of claim 22 wherein said yoke extends from below said ends of said flanking arms, past the inward edges of said arms, and over said ends, thereby to retain said ends against sideward as well as upward movement.

24. The valve of claim 23 wherein said yoke is U-shaped so as to pass between said central arm and said flanking arms.

25. The valve of claim 24 wherein each of said ends of said flanking arms have a notch receiving that portion of said yoke passing said inward adges of said arms, thereby to retain said spring against longitudinal movement as well as upward and sideward movement.

26. The valve of claim 23 wherein said yoke is not fastened to said ends of said flanking arms but fits loosely thereover.

27. The valve of claim 1 wherein said primary member comprises a toothed gear mounted for rotation and said secondary member comprises an escapement element engaging the teeth of said gear and a permanent magnet for moving said escapement element in response to said applied pulsed magnetic field to thereby rotate said toothed gear.

28. The valve of claim 22 wherein said cam or screw means comprises a screw extending through said spring portion.

29. The valve of claim 22 wherein said cam or screw means comprises a cam surface adapted to lift said spring portion as said gear is rotated.

30. The valve of claim 22 wherein said escapement element has blunt teeth of a shape that mates with the teeth of said gear.

31. The valve of claim 22 wherein said escapement element has teeth in the form of long, thin elements adapted for piercing through debris collected between the teeth of said gear.

32. The valve of claim 22 wherein said escapement element has two teeth.

33. A surgically-implantable shunt valve for venting cerebrospinal fluid in the treatment of hydrocephalus and for shunting other body fluids, said valve comprising a housing constructed of a surgically-implantable material, an inlet and outlet chamber within said housing, said housing including inlet and outlet ports communicating with said inlet and outlet chambers respectively for connecting said inlet and outlet chambers to external catheters or other fluid conduits, an aperture communicating between said chambers, said aperture having a circular periphery forming a circular valve seat, a valve element of diameter larger than said circular valve seat, spring means for biasing said valve element against the circular valve seat so as to keep said aperture closed until the cerebrospinal fluid pressure in said inlet chamber exceeds a preselected popping pressure and so as to open said aperture when said popping pressure is exceeded so as to vent cerebrospinal fluid through said aperture into said outlet chamber, and incremental magnetic adjustment means for increasing or decreasing the amount of said bias in finite increments in response to pulses of an applied magnetic field so as thereby to increase or decrease said popping pressure in finite increments, said incremental magnetic adjustment means comprising an element adapted to rotate in response to an external magnetic field and wherein said valve further comprises a cam in the shape of a circular staircase and wherein said spring means includes one arm supported on said staircase.

* * * * *

UNITED STATES PATENT AND TRADEMARK OFFICE
CERTIFICATE OF CORRECTION

PATENT NO.    : 4,595,390

DATED         : June 17, 1986

INVENTOR(S)   : Hakim, et al.

It is certified that error appears in the above-identified patent and that said Letters Patent is hereby corrected as shown below:

Column 6, line 48, "valVe" should be --valve--.
Column 14, claim 1, line 60, "ao" should be --so--.

Column 16, claim 20, line 30, after "rate" should be --(K factor)--.
Column 17, claim 25, line 1, "adges" should be --edges--.

Signed and Sealed this

Twenty-fifth Day of February, 1992

Attest:

HARRY F. MANBECK, JR.

*Attesting Officer*  *Commissioner of Patents and Trademarks*